US008515525B2

(12) United States Patent
DeRobertis

(10) Patent No.: US 8,515,525 B2
(45) Date of Patent: Aug. 20, 2013

(54) SKIN ADHESIVE AGENT FOR MAMMOGRAPHY PROCEDURES

(75) Inventor: Nancy DeRobertis, Cresskill, NJ (US)

(73) Assignee: Women's Imaging Solutions Enterprises LLC, Cresskill, NJ (US)

( * ) Notice: Subject to any disclaimer, the term of this patent is extended or adjusted under 35 U.S.C. 154(b) by 5 days.

(21) Appl. No.: 13/211,013

(22) Filed: Aug. 16, 2011

(65) Prior Publication Data

US 2012/0016223 A1 Jan. 19, 2012

(51) Int. Cl.
*A61B 5/05* (2006.01)

(52) U.S. Cl.
USPC .......................................... 600/415; 600/407

(58) Field of Classification Search
USPC ............................. 600/407–429, 437; 604/20
See application file for complete search history.

(56) References Cited

U.S. PATENT DOCUMENTS

| | | | | |
|---|---|---|---|---|
| 5,021,327 A * | 6/1991 | Bunch et al. | | 430/496 |
| 5,023,107 A | 6/1991 | Roberts | | |
| 5,965,318 A * | 10/1999 | Goedeweeck et al. | | 430/139 |
| 6,200,743 B1 * | 3/2001 | Elst et al. | | 430/576 |
| 6,214,531 B1 * | 4/2001 | Elst et al. | | 430/567 |
| 6,277,552 B1 * | 8/2001 | Elst et al. | | 430/567 |
| 6,573,019 B1 * | 6/2003 | Van den Zegel et al. | | 430/139 |
| 6,613,755 B2 | 9/2003 | Peterson et al. | | |
| 6,686,142 B2 * | 2/2004 | Elst et al. | | 430/567 |
| 6,689,787 B1 * | 2/2004 | McKearn et al. | | 514/275 |
| 6,733,947 B2 * | 5/2004 | De Bie et al. | | 430/139 |
| 6,833,373 B1 * | 12/2004 | McKearn et al. | | 514/272 |
| 6,858,598 B1 * | 2/2005 | McKearn et al. | | 514/183 |
| 6,916,800 B2 * | 7/2005 | McKearn et al. | | 514/183 |
| 7,792,244 B2 | 9/2010 | DeFreitas et al. | | |
| 8,039,501 B2 * | 10/2011 | Vanden Berghe et al. | | 514/399 |
| 2002/0037310 A1 | 3/2002 | Jonn et al. | | |
| 2002/0192607 A1 * | 12/2002 | Elst et al. | | 430/567 |
| 2003/0091620 A1 | 5/2003 | Fikstad et al. | | |
| 2003/0203956 A1 * | 10/2003 | Masterrer | | 514/406 |
| 2004/0009423 A1 * | 1/2004 | Bie et al. | | 430/139 |
| 2004/0127470 A1 * | 7/2004 | Masferrer | | 514/165 |
| 2004/0234624 A1 * | 11/2004 | McKearn et al. | | 424/649 |
| 2005/0033157 A1 * | 2/2005 | Klein et al. | | 600/411 |
| 2005/0037090 A1 * | 2/2005 | McKearn et al. | | 424/649 |
| 2005/0058725 A1 * | 3/2005 | McKearn et al. | | 424/687 |
| 2005/0214236 A1 | 9/2005 | Peng et al. | | |
| 2005/0288581 A1 | 12/2005 | Kapur et al. | | |
| 2007/0059769 A1 * | 3/2007 | Blixt et al. | | 435/7.1 |
| 2007/0066552 A1 * | 3/2007 | Clarke et al. | | 514/44 |
| 2007/0240247 A1 | 10/2007 | Beck | | |
| 2007/0298091 A1 | 12/2007 | Kugelmann et al. | | |

(Continued)

OTHER PUBLICATIONS

International Search Report of PCT/US12/50585 dated Oct. 23, 2012.

(Continued)

*Primary Examiner* — Sanjay Cattungal
(74) *Attorney, Agent, or Firm* — Amster, Rothstein & Ebenstein LLP; Philip H. Gottfried, Esq.

(57) ABSTRACT

A method of examining breast tissue of a patient's breast using a mammography machine including the steps of manipulating the patient's breast so that at least a portion of the patient's breast is positioned for examination by the mammography machine, the manipulation being facilitated by a skin adhesive agent comprising a quaternary ammonium compound, and examining the breast tissue of the positioned patient's breast using the mammography machine.

4 Claims, 7 Drawing Sheets

(56) References Cited

U.S. PATENT DOCUMENTS

| | | | |
|---|---|---|---|
| 2008/0019968 A1* | 1/2008 | Blixt et al. | 424/138.1 |
| 2008/0091233 A1 | 4/2008 | Ellis-Behnke et al. | |
| 2008/0132474 A1* | 6/2008 | Coopersmith et al. | 514/171 |
| 2009/0005722 A1* | 1/2009 | Jennlngs-Spring | 604/20 |
| 2009/0135997 A1 | 5/2009 | Defreitas et al. | |
| 2010/0029734 A1* | 2/2010 | White et al. | 514/381 |
| 2010/0121304 A1* | 5/2010 | Zhou et al. | 604/387 |
| 2010/0198177 A1* | 8/2010 | Yahiaoui et al. | 604/359 |
| 2010/0269749 A1 | 10/2010 | Badejo et al. | |
| 2011/0034796 A1 | 2/2011 | Ma et al. | |

OTHER PUBLICATIONS

Written Opinion of the International Searching Authority dated Oct. 23, 2012.

\* cited by examiner

SKIN ADHESIVE AGENT FOR MAMMOGRAPHY PROCEDURES

FIELD OF THE INVENTION

The present disclosure relates to skin treatment agents, and in particular to skin treatment agents that facilitates the manipulation of a patient's breast so that more of the breast may be examined during a mammography procedure.

SUMMARY OF THE INVENTION

According to an exemplary embodiment of the present invention, a method of examining breast tissue of a patient's breast using a mammography machine comprises the steps of: manipulating the patient's breast so that at least a portion of the patient's breast is positioned for examination by the mammography machine, the manipulation being facilitated by a skin adhesive agent comprising a quaternary ammonium compound; and examining the breast tissue of the positioned patient's breast using the mammography machine.

A skin adhesive agent according to an exemplary embodiment of the present invention is used for manipulation of a patient's breast so that at least a portion of the patient's breast is positioned for examination by a mammography machine, and the skin adhesive agent comprises a quaternary ammonium compound.

According to at least one embodiment, the quaternary ammonium compound is at least one of benzalkonium chloride, benzethonium chloride, cetrimonium bromide, methylbenzethonium chloride, cetalkonium chloride, dofanium chloride, and domiphen bromide.

According to at least one embodiment, the skin adhesive agent is in the form of a powder.

According to at least one embodiment, the skin adhesive agent is an aqueous solution.

These and other features of this invention are described in, or are apparent from, the following detailed description of various exemplary embodiments of this invention.

BRIEF DESCRIPTION OF THE DRAWINGS

The features and advantages of the present invention will be more fully understood with reference to the following, detailed description of an illustrative embodiment of the present invention when taken in conjunction with the accompanying figures, wherein.

DETAILED DESCRIPTION OF EMBODIMENTS OF THE PRESENT INVENTION

Breast cancer is currently the most common type of cancer in women. In the early stages, breast cancer does not typically cause symptoms, so regular screening of breast tissue is critical. One type of early screening procedure involves examination of the breast tissue using a mammography machine. A mammography machine includes two radiographic breast supports (one support known as the "bucky" and the other support being the compression paddle), and the procedure requires the patient's breasts to be placed between the supports so that an X-ray image of the breasts may be taken. In order to maximize detection of all cancerous tissue within the breast, it is critical for the clinician to have the ability and skill to manipulate and properly position the breast within the mammography machine. The clinician must be able to grip, manipulate and hold the breast between the supports while the supports are pressed together to flatten the breast.

Fear of medical malpractice suits has steered many radiologists from the mammography field and leave many fellowships in mammography vacant. Misdiagnosis of cancer, particularly breast cancer, accounts for the primary reason why radiologists are sued. Although a high level of skill is required for a radiologist to ensure that a patient's breast is properly screened by the mammography machine, the radiologist is also limited by simple human anatomy. In this regard, the radiologist risks being sued if a cancer is not detected due to the clinician's failure to properly position the patient's breast within the mammography machine, which may have resulted not from the alleged lack of skill of the clinician, but instead from the awkward physical challenges faced by the clinician in manipulating as much of the breast tissue as possible within a sensitive diagnostic machine.

In order to facilitate proper positioning of a patient's breast within a mammography machine, various exemplary embodiments of the present invention provide a skin adhesive agent that may be applied to the clinician's hands prior to the clinician's contact with the patient's breast. The skin adhesive agent may be a quaternary ammonium compound, also known as a "quat", such as, for example, benzalkonium chloride, benzethonium chloride, cetrimonium bromide, methylbenzethonium chloride, cetalkonium chloride, dofanium chloride, domiphen bromide or mixture thereof. The skin adhesive agent may also include a non-alcoholic base. The skin adhesive agent leaves the hands slightly sticky before completely drying, which increases the adhesiveness of the clinician's hands relative to the patient's breast. This in turn maximizes the amount of breast tissue that may pulled onto an image.

Figure 1:
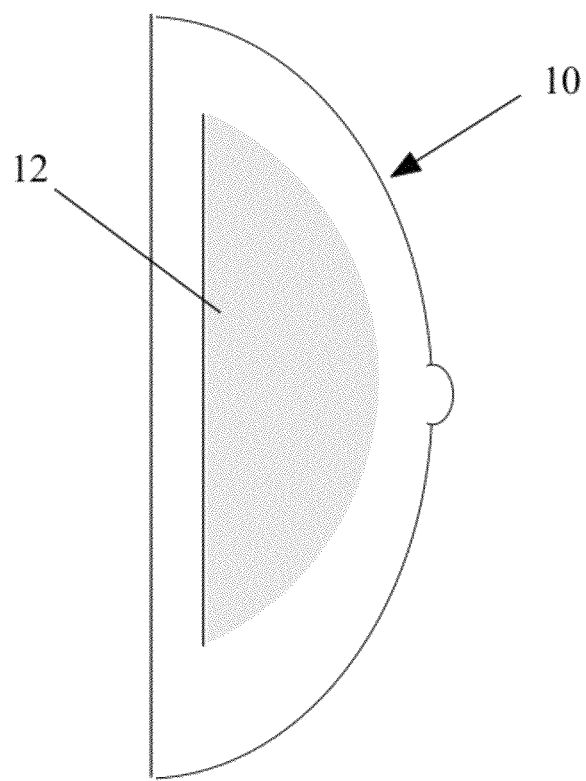
FIG. 1 is a schematic representation of the cross-section of a human breast.

Many breast cancers develop at the periphery of the parenchyma beneath the interface between the subcutaneous fat or retromammary fat and the parenchymal cone of the breast. As shown in the schematic of FIG. 1, this peripheral region 12 of the breast 10 includes an area close to the chest wall. More than 70% of breast cancers detected by mammography lie in this zone alone. Thus, a clinician's ability to pull the breast off the chest wall so that breast tissue within this peripheral zone may be clearly viewed by the mammography machine is critical in ensuring that no cancerous tissue is overlooked. In this regard, the skin adhesive agent according to various exemplary embodiments of the present invention is particularly effective in increasing the amount of breast tissue that can be manipulated during a mammography procedure, particularly the breast tissue within the posterior peripheral zone near the chest wall. A comparison between results of mammography exams in which the inventive skin adhesive agent was used against mammography exams performed without the use of the inventive skin adhesive agent have shown that the inventive skin adhesive agent enables for the examination of up to 3 cm more breast tissue. Acquiring a 3 cm difference is particularly critical given the fact that the average breast cancer size found on a mammogram is 1.1. cm, and the smallest size of breast cancers visible on a mammogram are between 0.2 and 0.3 cm.

The following examples illustrate the effectiveness of the adhesive agent according to various exemplary embodiments of the present invention:

Example 1

Figures 2A, 2B:
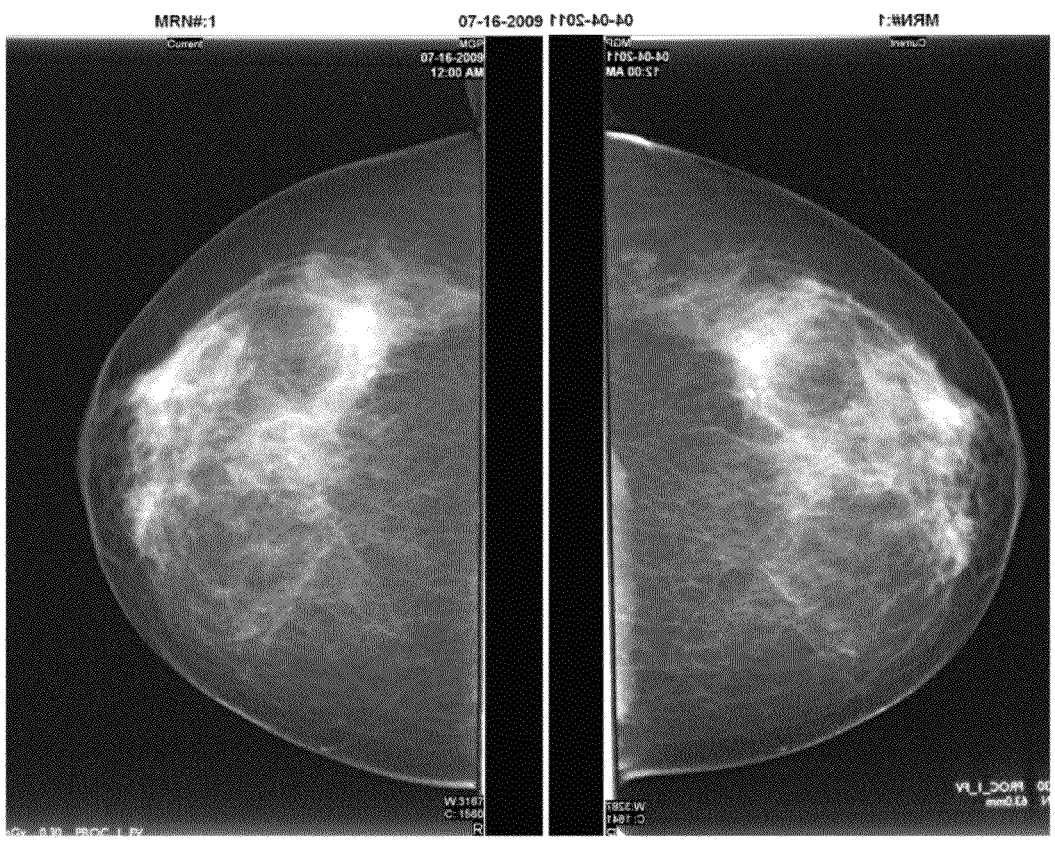
FIGS. 2A and 2B are mammographic images of a patient's breast showing the effectiveness of the adhesive agent according to an exemplary embodiment of the present invention.

FIG. 2A shows mammography image results of a patient's breast after the mammography exam was performed without the inventive adhesive agent. Without the adhesive agent, 11.1 cm of breast tissue was able to be imaged. FIG. 2B shows the mammography image results of the same patient's breast obtained using the adhesive agent. With the adhesive agent, 12.1 cm of breast tissue was able to be imaged. In this example, up to 10 mm more breast tissue was imaged by using the adhesive agent, resulting in the exposure of a new area of nodularity.

Example 2

Figures 3A, 3B:
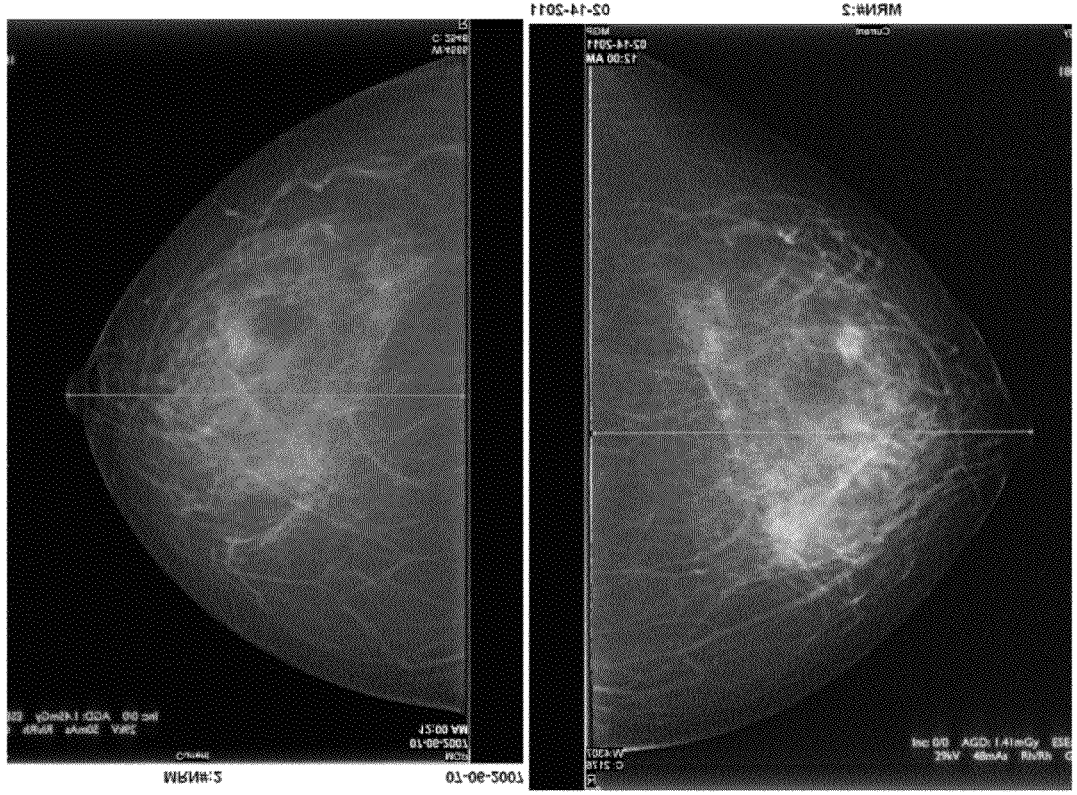
FIGS. 3A and 3B are mammographic images of a patient's breast showing the effectiveness of the adhesive agent according to an exemplary embodiment of the present invention.

FIG. 3A shows the mammography image results of a patient's breast after the mammography exam was performed without the inventive adhesive agent. Without the adhesive agent, 13 cm of breast tissue was able to be imaged. FIG. 2B shows the mammography image results of the same patient's breast obtained using the adhesive agent. With the adhesive agent, 14 cm of breast tissue was able to be imaged. In this example, up to 10 mm more breast tissue was imaged by using the adhesive agent, resulting in the exposure of a possible new mass. This example illustrates how the adhesive agent results in acquisition of more breast tissue, which in turn results in better compression and a sharper, more detailed image.

Example 3

Figures 4A, 4B:
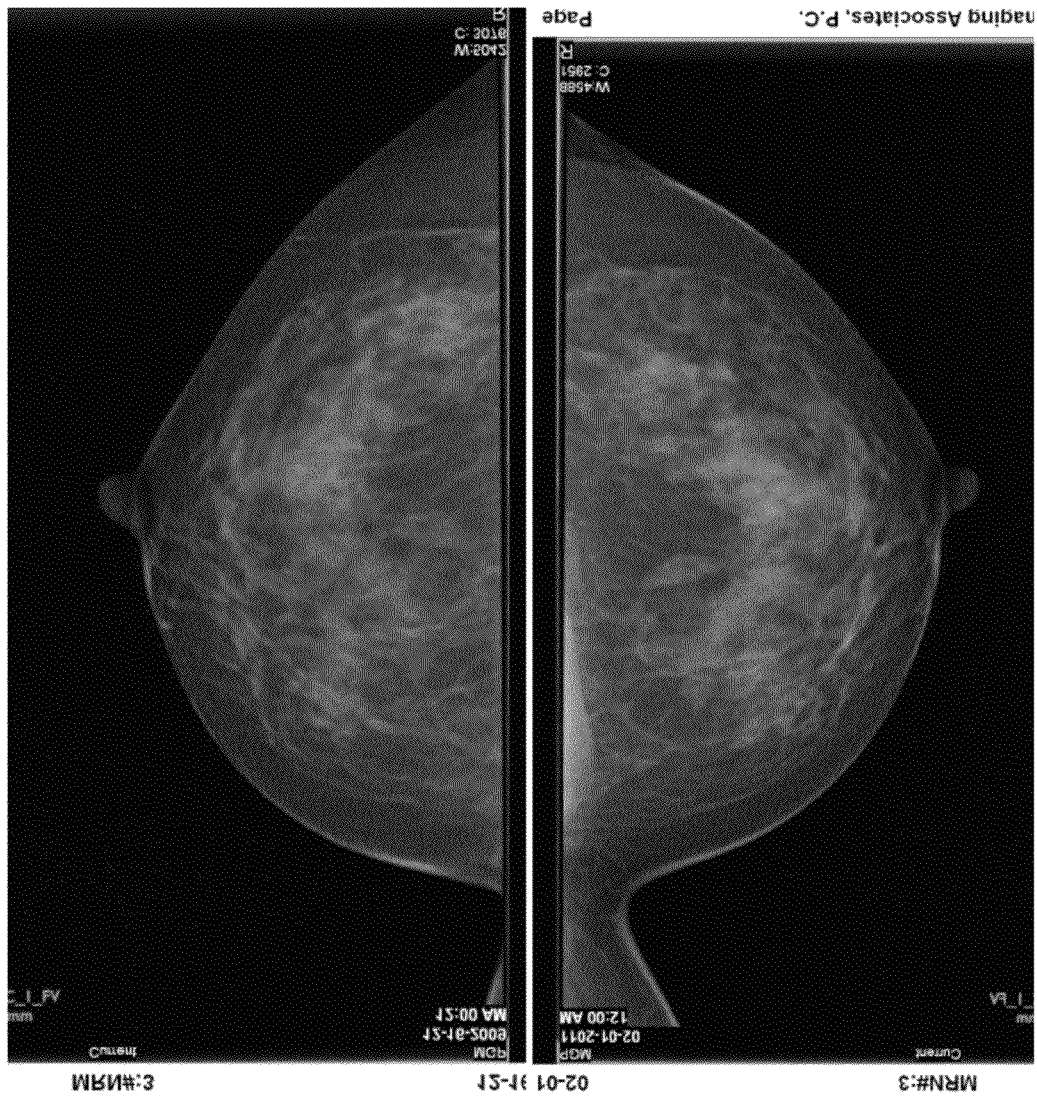
FIGS. 4A and 4B are mammographic images of a patient's breast showing the effectiveness of the adhesive agent according to an exemplary embodiment of the present invention.

FIG. 4A shows mammography image results of a patient's breast after the mammography exam was performed without the inventive adhesive agent. Without the adhesive agent, 8 cm of breast tissue was able to be imaged. FIG. 4B shows the mammography image results of the same patient's breast obtained using the adhesive agent. With the adhesive agent, 8.8 cm of breast tissue was able to be imaged.

Example 4

Figures 5A, 5B:
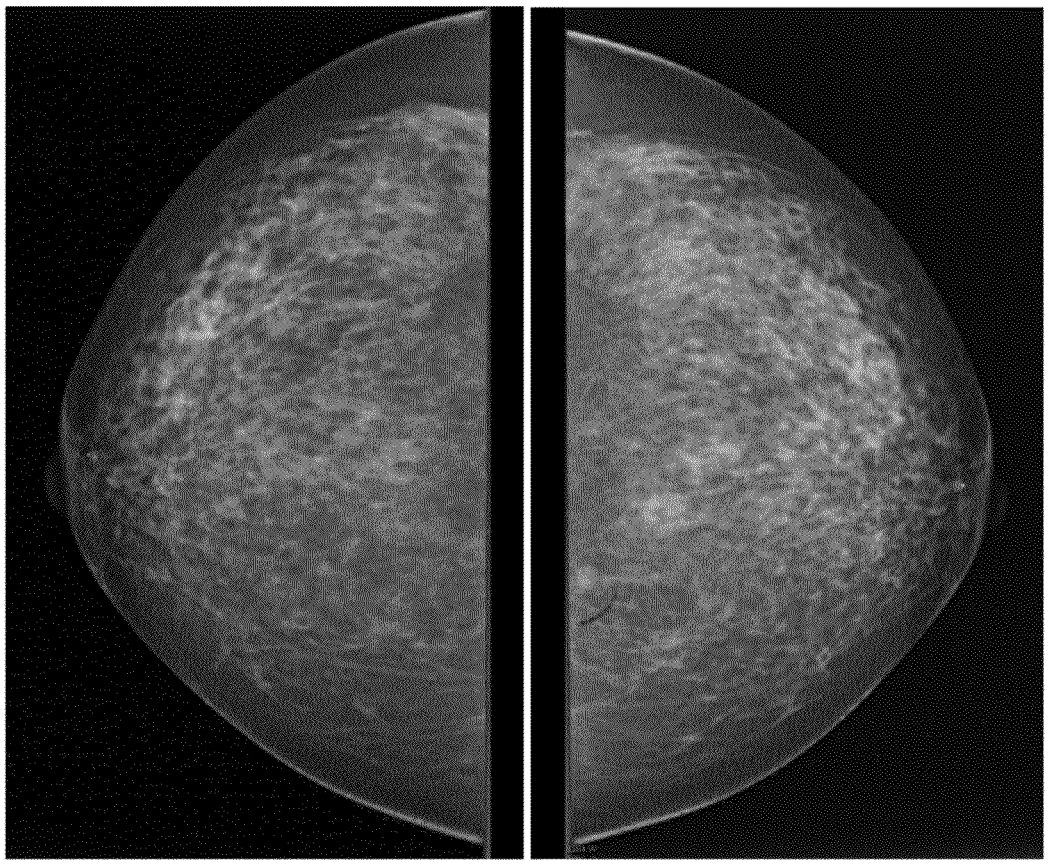
FIGS. 5A and 5B A are mammographic images of a patient's breast showing the effectiveness of the adhesive agent according to an exemplary embodiment of the present invention.

FIG. 5A shows mammography image results of a patient's breast after the mammography exam was performed without the inventive adhesive agent. Without the adhesive agent, 9.5 cm of breast tissue was able to be imaged. FIG. 2B shows the mammography image results of the same patient's breast obtained using the adhesive agent. With the adhesive agent, 10.5 cm of breast tissue was able to be imaged. In this particular example, the enhanced image obtained using the adhesive agent lead to the detection of a new mass, and the patient underwent a lumpectomy, possibly saving the patient's life.

Example 5

Figures 6A, 6B:
FIGS. 6A and 6B are mammographic images of a patient's breast showing the effectiveness of the adhesive agent according to an exemplary embodiment of the present invention.

FIG. 6A shows mammography image results of a patient's breast after the mammography exam was performed without the inventive adhesive agent. Without the adhesive agent, 7.6 cm of breast tissue was able to be imaged. FIG. 2B shows the mammography image results of the same patient's breast obtained using the adhesive agent. With the adhesive agent, 8.5 cm of breast tissue was able to be imaged.

Example 6

Figures 7A, 7B:
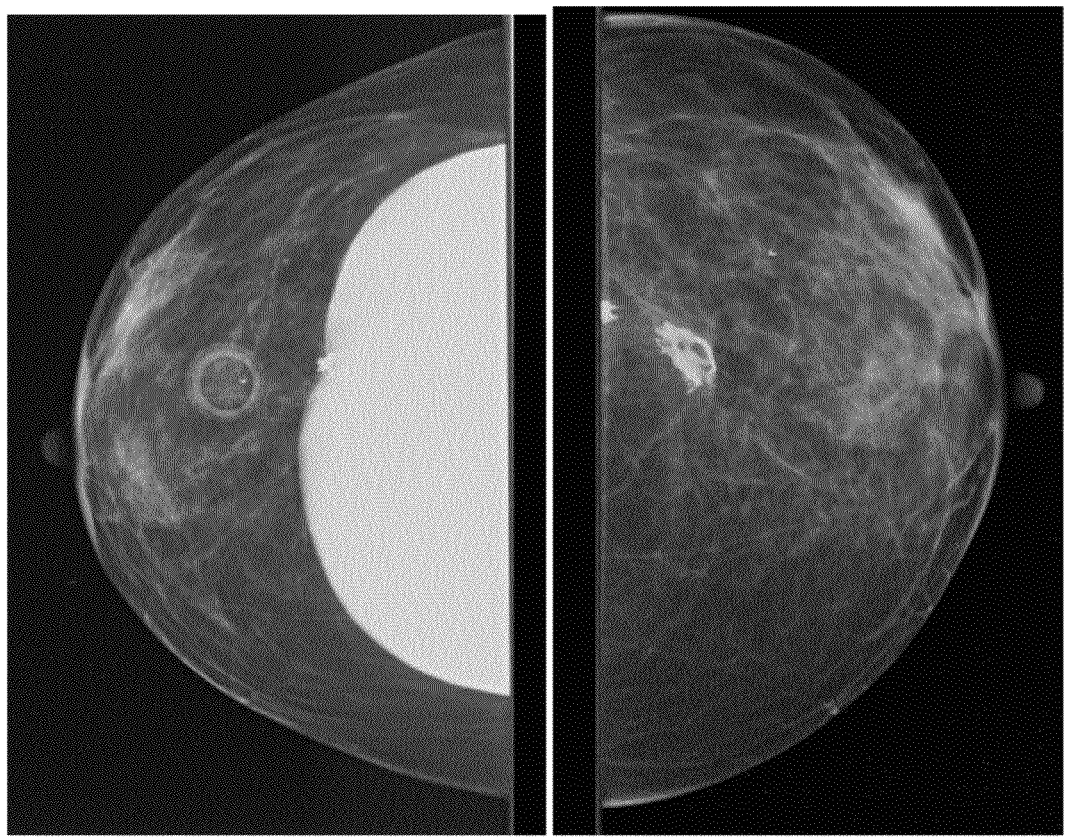
FIGS. 7A and 7B are mammographic images of a patient's breast showing the effectiveness of the adhesive agent according to an exemplary embodiment of the present invention.

FIG. 7A shows mammography image results of a patient's breast after the mammography exam was performed without the inventive adhesive agent. Without the adhesive agent, 5.5 cm of breast tissue was able to be imaged. FIG. 2B shows the mammography image results of the same patient's breast obtained using the adhesive agent. With the adhesive agent, 8.5 cm of breast tissue was able to be imaged. In this example, 3 cm more breast tissue was imaged by using the adhesive agent. This amount is almost three times more than the average size of breast cancers and at least five times more than the smallest visible cancers seen on a mammogram.

In other examples, use of the inventive adhesive agent resulted in increased imaged breast tissue in the amounts of 10 mm, 12 mm, 9 mm, 20 mm, 5.6 mm, 15 mm, 12 mm, and 20 mm.

According to various exemplary embodiments of the present invention, the skin adhesive agent may be made available to the clinician in powder form to decrease shipping costs. The clinician may then mix the powder with water to produce an aqueous solution that can be sprayed or otherwise applied to the clinician's hands prior to the mammography exam. In other exemplary embodiments, the skin adhesive agent may be pre-packaged as an aqueous solution. In addition to the active quat, the skin adhesive agent may include inactive ingredients, such as, for example, water, anti-static agents such as dihydroxypropyl PEG-5 linoleammonium chloride, emulsifying agents such as glycereth 2 cocoate, disinfectant agents such as behentrimonium chloride, cleaning agents such as dihydroxy ethyl cocoamine oxide, fragrance and/or coloring agents. The skin adhesive agent is preferably non-alcoholic. In an exemplary embodiment of the present invention, 0.1 wt % of active ingredient is present in the aqueous solution that forms the adhesive agent.

Now that embodiments of the present invention have been shown and described in detail, various modifications and improvements thereon will become readily apparent to those skilled in the art. Accordingly, the spirit and scope of the present invention is to be construed broadly and limited only by the appended claims and not by the foregoing specification.

What is claimed is:

1. A method of examining breast tissue of a patient's breast using a mammography machine comprising the steps of:
    manipulating the patient's breast so that at least a portion of the patient's breast is positioned for examination by the mammography machine, the manipulation being facilitated by a skin adhesive agent comprising a quaternary ammonium compound; and
    examining the breast tissue of the positioned patient's breast using the mammography machine.

2. The method of claim 1, wherein the quaternary ammonium compound is at least one of benzalkonium chloride, benzethonium chloride, cetrimonium bromide, methylbenzethonium chloride, cetalkonium chloride, dofanium chloride, and domiphen bromide.

3. The method of claim 1, wherein the skin adhesive agent is in the form of a powder.

4. The method of claim 1, wherein the skin adhesive agent is an aqueous solution.

* * * * *